US005455350A

United States Patent [19]
Godek et al.

[11] Patent Number: 5,455,350
[45] Date of Patent: Oct. 3, 1995

[54] PROCESS AND INTERMEDIATE FOR CERTAIN BIS-AZA-BICYCLIC ANXIOLYTIC AGENTS

[75] Inventors: Dennis M. Godek, Glastonbury; Charles W. Murtiashaw, North Stonington; Frank J. Urban, Waterford; Brian C. Vanderplas, Niantic, all of Conn.

[73] Assignee: Pfizer Inc., New York, N.Y.

[21] Appl. No.: 137,049

[22] Filed: Oct. 13, 1993

[51] Int. Cl.⁶ .................. C07D 471/04; C07D 227/00
[52] U.S. Cl. ............................. 544/349; 546/272
[58] Field of Search ................................ 544/349

[56] References Cited

U.S. PATENT DOCUMENTS 3,388,128  6/1968  Day ............................................ 260/268

FOREIGN PATENT DOCUMENTS 380217   8/1990  European Pat. Off. .
9008144  7/1990  WIPO .
93-23404 11/1993  WIPO ................................. 544/349
93-25552 12/1993  WIPO ................................. 544/349

OTHER PUBLICATIONS

J. March, Advanced Organic Chemistry, 4th Ed., p. 426 (1992).
Wolfe et al., Canadian Journal of Chemistry, 48 (19), 3572–3579 (1970).

Primary Examiner—Mark L. Berch
Attorney, Agent, or Firm—Peter C. Richardson; Paul H. Ginsburg; Bryan C. Zielinski

[57] ABSTRACT

($C_1$–$C_3$)Alkyl-4,6,7,8,9,9a-hexahydro-2H,3H-pyrido[1,2-a]pyrazin-1-one-7-carboxylate esters, important precursors to certain bis-aza-bicyclic anxiolytics, can be prepared from di($C_1$–$C_3$)alkyl cis-piperidine-2,5-dicarboxylate starting material by a new process via a new class of intermediates, di($C_1$–$C_3$)alkyl cis-N-(2-(phthalimido)ethyl)piperidine-2,5-dicarboxylates. In the process, the starting material is reacted with either 2-(phthalimido)ethyl triflate or 2-(phthalimido)acetaldehyde to form the new intermediate, which can then be cyclized to the aforementioned precursor.

12 Claims, No Drawings

PROCESS AND INTERMEDIATE FOR CERTAIN BIS-AZA-BICYCLIC ANXIOLYTIC AGENTS

This application to a 371 of PCT VS 91/08400, Nov. 19, 1991.

BACKGROUND OF THE INVENTION

The present invention is directed to di($C_1$–$C_3$)alkyl cis-N-(2-(phthalimido)ethyl)piperidine-2,5-dicarboxylate esters of the formula (II) below, and to processes which employ this compound as an intermediate in the conversion of a di($C_1$–$C_3$)alkyl cis-piperidine-2,5-dicarboxylate (of the formula (I) below) to a racemic ($C_1$–$C_3$)alkyl (7S*,9aS*)-4,6,7,8,9,9a-hexahydro-2H,3 H-pyrido[1,2-a]pyrazin-1-one-7-carboxylate ester (of the formula (III) below). The structural diagrams and the R* and S* symbols employed herein are intended to designate relative, not absolute, stereochemistry.

Compounds of the formula (III) are known, having been previously described by Bright et al. as intermediates useful in the synthesis of certain bis-aza-bicyclic anxiolytic agents of the formula

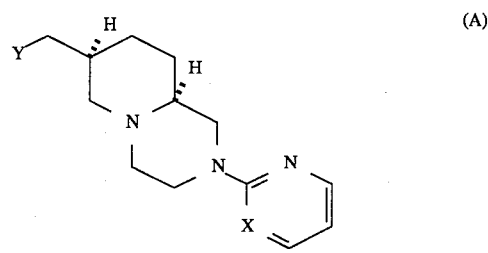

(A)

wherein X is N or CH and Y represents one of certain pyrazolo, triazolo, tetrazolo or cyclic imido radicals, in International Patent Application published under the Patent Cooperation Treaty (PCT), International Publication No. WO 90/08144, July, 1990.

Preparation of isomeric ($C_1$–$C_3$)alkyl (7R*,9aS*)-4,6,7,8,9,9a-hexahydro-2H,3H-pyrido[1,2-a]pyrazin-1-one-7-carboxylate esters from di($C_1$–$C_3$)alkyl transpiperidine-2,5-dicarboxylate via analogous processes and intermediates is described in concurrently filed U.S. patent application Ser. No. 07/661,726, ABN by Urban for "Process for trans-Piperidine-2,5-dicarboxylates."

SUMMARY OF THE INVENTION

The present invention is directed to processes as follows:

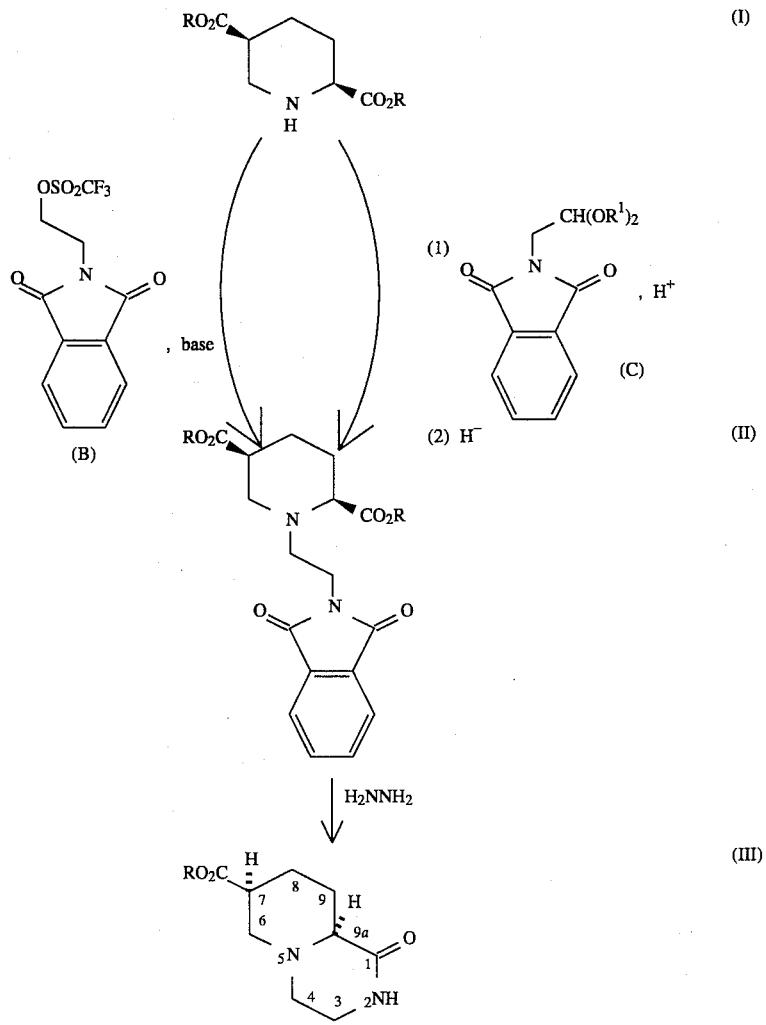

wherein R and R[1] are each independently $(C_1$–$C_3)$alkyl. The preferred value of R is methyl, and the preferred value of R[1] is ethyl.

The present invention is also directed to the intermediate of the formula (II), preferably with R as methyl.

As used hereinafter, the expression "reaction inert solvent" refers to a solvent system in which the components do not interact with starting materials, reagents, intermediates or products in a manner which adversely affects the yield of the desired product.

DETAILED DESCRIPTION OF THE INVENTION

The present invention is readily carried out. The dialkyl cis-piperidine-2,5-dicarboxylate ester (I) used as starting material is known and generally obtained by conventional catalytic hydrogenation methods from the corresponding dialkyl pyridine-2,5-dicarboxylate.

According to one variation of the first stage of the process of the present invention, the intermediate compound of the formula (II) is formed by reacting the compound of the formula (I) with 2-(phthalimido)ethyl triflate (reagent B depicted above). Generally, at least one molar equivalent (usually about 2–15% molar excess) of this reagent is employed, in the presence of a base, such as sodium carbonate (again, generally at least one molar equivalent, but usually a 2–4 fold molar excess). The reaction is carried out in a reaction inert solvent, preferably a biphasic solvent comprising water and a water-immiscible solvent such as methylene chloride. Reaction temperature is not critical, with temperatures in the range of from about 5° C. to 45° C. being generally satisfactory. Ambient temperatures (e.g. about 17°–28° C.) are preferred, since the energy costs of heating or cooling the reaction mixture are avoided. The product of formula (II) is readily isolated by conventional methods from the organic phase of the reaction mixture.

According to an alternative variation of the first stage of the present invention, the N-(2-(phthalimido)ethyl) group is introduced by reductive alkylation of the compound (I) with 2-(phthalimido)acetaldehyde, in the presence of hydrogen and a hydrogenation catalyst, or preferably in the presence of a hydride reducing agent. The required aldehyde is conveniently formed in situ by the acid catalyzed hydrolysis of commercially available 2-(phthalimido) acetaldehyde diethyl acetal (R[1]=ethyl; reagent C depicted above). According to the preferred method, the diester (I) is generally prereacted with this in situ formed aldehyde, still in the presence of the strong acid catalyst (e.g., HCl) used for the hydrolysis of the acetal. The resulting adduct is then reduced with a hydride reducing agent, preferably a mild reagent such as sodium triacetoxyborohydride [Na(OAc)$_3$BH] in a reaction inert solvent, such as acetic acid, still in the presence of the excess strong acid used to hydrolyze the acetal. Temperature is not critical, with temperatures in the range of about 15°–40° C. being generally satisfactory. The product of formula (II) is readily isolated by conventional methods from an extract of the reaction mixture with a water immiscible solvent such as methylene chloride.

The second stage of the process of the present invention, in which the intermediate of the formula (II) is cyclized to form the desired alkyl pyrido[1,2-a]pyrazin-1-one-7-carboxylate derivative of the formula (III), is conveniently accomplished by the action of a primary amine such as methylamine, or aqueous hydrazine, in a reaction inert solvent such as methanol. The preferred reagent is hydrazine, since it leads to an insoluble by-product which is readily removed by simple filtration. At least one molar equivalent of hydrazine is employed, usually two or more molar equivalents. Temperature is not critical, with temperatures in the 5°–45° C. range being generally satisfactory, with ambient temperatures, for reasons as noted above, being preferred.

As noted above, the compounds of the formula (III) are useful as intermediates in the manufacture of anxiolytic agents of the above formula (A) according to the methods of Bright et al., WO 90/08144, cited above.

The following examples are provided solely for the purpose of further illustration.

EXAMPLE 1

Dimethyl cis-N-(2-(phthalimido)ethyl)piperidine- 2,5-dicarboxylate

Method A

A solution of 12.0 g (45.6 mmol) phthalimido acetaldehyde diethyl acetal (Aldrich Chemical Co., Inc.) in 36 ml acetic acid and 1.34 ml concentrated HCl was heated at 45°–50° C. for 2 hours. After cooling the solution to 20° C., 9.08 g dimethyl cis-piperidine-2,5-dicarboxylate was added and stirring was continued for an additional 30 minutes at 20°–25° C. The resulting light orange solution was treated with the portionwise addition of 12.08 g (57 mmol) Na(OAc)$_3$BH over 30 minutes and stirred for an additional 30 minutes at 30°–35° C. The solution was cooled to 20° C. and diluted with 120 ml H$_2$O and 120 ml CH$_2$Cl$_2$ followed by shaking and separation of the phases. The organic phase was washed first with 50 ml H$_2$O and then 50 ml saturated NaHCO$_3$. Distillative displacement of the CH$_2$Cl$_2$ with 36 ml EtOH, followed by the addition of 100 ml hexanes, resulted in the crystallization of a solid which was allowed to granulate overnight at 20°–25° C. Filtration and drying of this solid provided 13.5 g (79.4%) of present title product as a solid melting at 97°–100° C.

Method B

A stirred mixture of 70 ml of CH$_2$Cl$_2$, 9.8 g (51 mmol) of N-(2-hydroxyethyl) phthalimide and 6.1 ml (0.52 mmol) of 2,6-lutidine was cooled to −4° C. Maintaining the temperature below 15° C., trifluoromethane sulfonic anhydride (8.9 ml, 0.53 mmol) was added slowly over 1 hour. The resulting mixture was stirred at 15°–20° C. for 1.25 hours, then washed sequentially with 40 ml H$_2$O, 40 ml 2N HCl and 40 ml H$_2$O to yield a solution of N-((2-triflyloxy)ethyl)phthalimide. At 20°–25° C., a separate reaction vessel was charged with 50 ml CH$_2$Cl$_2$, 55 ml H$_2$O and 10.6 g (0.1 mol) Na$_2$CO$_3$. After stirring for 15 minutes, dimethyl cis-piperidine-2,5-dicarboxylate (11.9 g, 50 mmol) and the above reagent solution were added, and the mixture stirred for 1.25 hours at 20°–25° C. The organic layer was separated, washed with 30 ml of water, and the CH$_2$Cl$_2$ displaced by boiling with hexane to a final volume of 125 ml, during which time the present title product began to crystallize. After stirring and granulating for 1 hour at 0°–5° C., the present title product, 16.7 g, was recovered by filtration; m.p. 98°–100° C.

Method C

To a well-stirred bi-phasic mixture consisting of sodium carbonate (500 g, 4.72 mol) in water (3 liters) and cis-2,5-piperidine dicarboxylate dimethyl ester (240 g, 1.18 mol) in methylene chloride (4.5 liters), a solution of 2(phthalimido-)ethyl triflate (417 g, 1.29 mol) in methylene chloride (3 liters) is added in a steady stream over a 3 hour period. The organic layer is separated, and the aqueous layer is extracted with fresh methylene chloride (3 liters). The combined organic extracts are washed with water (3 liters), then with brine (3 liters), dried with anhydrous magnesium sulfate and finally concentrated in vacuo to a solid. The entire residue is triturated in refluxing ether (3 liters) with vigorous stirring for 15 minutes. After cooling to ambient temperature, the solution is poured into hexanes (3 liters), and the resulting mixture is stirred for 18 hours. The present title product is collected by filtration.

EXAMPLE 2

Racemic Methyl (7S*,9aS*)-4,6,7,8,9,9a-Hexahydro-2H, 3H-pyrido[1,2-a]pyrazin-1-one-7-carboxylate A mixture of 240 ml of methanol, 16.6 g (44 mmol) of the title product of Example 1, and 5.74 ml (97 mmol) of 54% hydrazine was stirred at 20°–25° C. for 17 hours. The mixture was then diluted with 200 ml of $CH_2Cl_2$, granulated for 1 hour, and by-product recovered by filtration with 75 ml $CH_2Cl_2$ wash. The combined filtrate and wash liquor was concentrated to 225 ml by distillation and $CH_2Cl_2$/methanol displaced with isopropyl alcohol by distillation to a final volume of 200 ml. After cooling slowly from 50° C. to 8° C. over a 2 hour period, title product, 9.2 g, was recovered by filtration. The entire batch was purified by recrystallization from $CH_2Cl_2$ to yield 7.45 g of purified title product, identical with the product of Preparation 4 of above cited Bright et al., WO90/08144.

We claim:

1. A process for the preparation of a compound of the formula

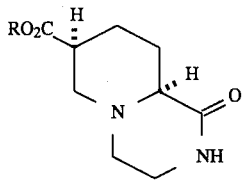

(III)

wherein R is $(C_1-C_3)$alkyl which comprises the steps of:

(a) reacting a compound of the formula

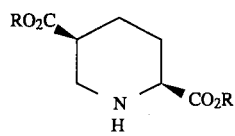

either with at least one molar equivalent of a triflate ester of the formula

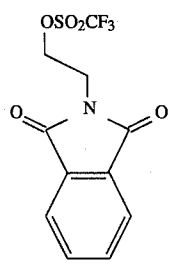

(B)

in the presence of molar excess of $Na_2CO_3$ in a biphasic reaction inert solvent comprising water and a water immiscible organic solvent, or with at least one molar equivalent of an aldehyde of the formula

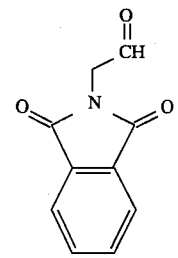

(C)

and at least one chemical equivalent of a hydride reducing agent, in a reaction inert solvent, to form an intermediate compound of the formula

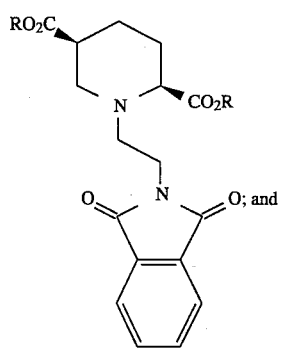

(II)

(b) cyclizing said compound of the formula (II) by the action of an excess of aqueous hydrazine in a reaction inert solvent to form said compound of the formula (III).

2. A process for the preparation of a compound of the formula

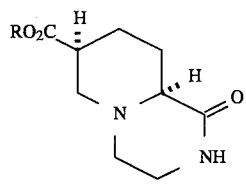

(III)

wherein R is $(C_1-C_3)$alkyl comprising:

(a) reacting a compound of the formula

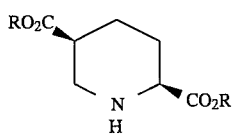

either with at least one molar equivalent of a triflate ester of the formula

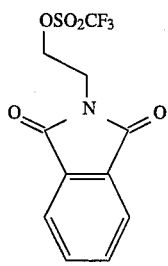
(B)

in the presence of molar excess of Na2CO3 in a biphasic reaction inert solvent comprising water and a water immiscible organic solvent, or with at least one molar equivalent of an aldehyde of the formula

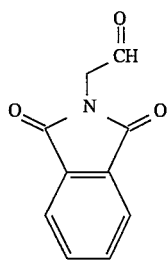
(C)

and at least one chemical equivalent of a hydride reducing agent, in a reaction inert solvent, to form an intermediate compound of the formula

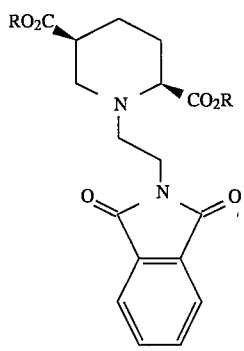
(II)

and (b) cyclizing said compound of the formula (II) by the action of an excess of a primary amine in a reaction inert solvent to form said compound of the formula (III).

3. The process of claim 2 wherein R is methyl.

4. A process of claim 1 wherein R is methyl.

5. A process of claim 4 wherein the reagent in step (a) is a triflate ester of the formula (B).

6. A process of claim 4 wherein the reagent in step (a) is an aldehyde of the formula (C).

7. A process of claim 6 wherein the aldehyde of the formula (C) is formed in situ by the acid catalyzed hydrolysis of an acetal of the formula

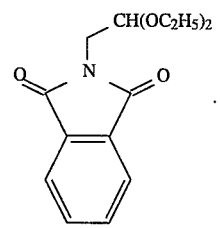

8. A process of claim 6 wherein the hydride reducing agent is sodium triacetoxyborohydride.

9. The process of claim 3 wherein the reagent in step (a) is a triflate ester of the formula (B).

10. The process of claim 3 wherein the reagent in step (a) is an aldehyde of the formula (C).

11. The process of claim 10 wherein the aldehyde of the formula (C) is formed in situ by the acid catalyzed hydrolysis of an acetal of the formula

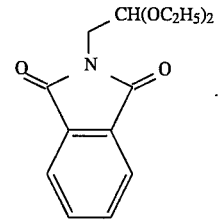

12. The process of claim 10 wherein the hydride reducing agent is sodium triacetoxyborohydride.

* * * * *